(12) United States Patent
Bilat et al.

(10) Patent No.: US 11,944,125 B2
(45) Date of Patent: Apr. 2, 2024

(54) SENSOR FOR DEVICE AEROSOL-GENERATING SYSTEM

(71) Applicant: Philip Morris Products S.A., Neuchatel (CH)

(72) Inventors: Stephane Bilat, Neuchatel (CH); Guillaume Colotte, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 425 days.

(21) Appl. No.: 17/296,635

(22) PCT Filed: Nov. 27, 2019

(86) PCT No.: PCT/EP2019/082777
§ 371 (c)(1),
(2) Date: May 25, 2021

(87) PCT Pub. No.: WO2020/109404
PCT Pub. Date: Jun. 4, 2020

(65) Prior Publication Data
US 2022/0015438 A1    Jan. 20, 2022

(30) Foreign Application Priority Data
Nov. 27, 2018    (EP) .................................... 18208667

(51) Int. Cl.
*A24F 40/51*    (2020.01)
*A24F 40/42*    (2020.01)
(Continued)

(52) U.S. Cl.
CPC .............. *A24F 40/51* (2020.01); *A24F 40/42* (2020.01); *A24F 40/53* (2020.01); *A24F 40/65* (2020.01)

(58) Field of Classification Search
CPC .......... A24F 40/51; A24F 40/53; A24F 40/65; A24F 40/42
(Continued)

(56) References Cited

U.S. PATENT DOCUMENTS 4,354,180 A    10/1982    Harding
7,164,849 B1    1/2007    Bankers et al.
(Continued)

FOREIGN PATENT DOCUMENTS

CN    103889488 A    6/2014
CN    105901769 A    8/2016
(Continued)

OTHER PUBLICATIONS

Combination Russian Office Action and Search Report dated Mar. 7, 2023 in Russian Patent Application No. 2021111754 (with English translation), 16 pages.
(Continued)

*Primary Examiner* — Gary F Paumen
(74) *Attorney, Agent, or Firm* — Oblon, McClelland, Maier & Neustadt, L.L.P.

(57) ABSTRACT

An aerosol-generating system is provided, including: a cartridge including a storage compartment configured to contain a liquid composition including an aerosol-forming substrate; an aerosol-generating device configured to receive the cartridge and including a power supply and control electronics operably coupled to the power supply; a light source operably coupled to the control electronics and positioned and oriented to emit light into the storage compartment, light emitted from the source is absorbed by the liquid composition; and a detector operably coupled to the control electronics and positioned and oriented to detect light emitted from the source, the source and the detector are both located adjacent to a same side of the storage compart-
(Continued)

ment, and a surface of the storage compartment opposite the source is configured to absorb light emitted into the storage compartment from the source.

19 Claims, 9 Drawing Sheets

(51) Int. Cl.
*A24F 40/53* (2020.01)
*A24F 40/65* (2020.01)
(58) Field of Classification Search
USPC .......................................................... 131/329
See application file for complete search history.

(56) References Cited

U.S. PATENT DOCUMENTS

| | | | |
|---|---|---|---|
| 10,238,149 B2 * | 3/2019 | Hon | A24F 40/51 |
| 10,477,896 B2 * | 11/2019 | Sur | G01F 23/292 |
| 10,609,959 B2 * | 4/2020 | Bilat | F22B 1/284 |
| 10,736,357 B2 * | 8/2020 | Hon | G01F 23/292 |
| 11,006,671 B2 * | 5/2021 | Li | A24F 40/50 |
| 2016/0345628 A1 * | 12/2016 | Sabet | H04M 1/21 |
| 2017/0042224 A1 | 2/2017 | Murison et al. | |
| 2017/0340009 A1 | 11/2017 | Hon | |
| 2017/0340010 A1 | 11/2017 | Bilat et al. | |
| 2017/0347710 A1 | 12/2017 | Hon | |
| 2018/0070632 A1 | 3/2018 | Sur et al. | |
| 2018/0098574 A1 | 4/2018 | Sur et al. | |
| 2018/0332895 A1 | 11/2018 | Li et al. | |

FOREIGN PATENT DOCUMENTS

| | | |
|---|---|---|
| CN | 107105773 A | 8/2017 |
| CN | 107183784 A1 | 9/2017 |
| EA | 029918 B1 | 5/2018 |
| EP | 2 286 190 A1 | 2/2011 |
| EP | 3 357 360 A2 | 8/2018 |
| EP | 3 357 360 A3 | 11/2018 |
| GB | 2533652 A | 6/2016 |
| GB | 2533653 A | 6/2016 |
| JP | 11-33097 A | 2/1999 |
| TW | 201811206 A | 4/2018 |
| WO | WO 97/048293 A1 | 12/1997 |
| WO | WO 2009/130235 A1 | 10/2009 |
| WO | WO 2015/127429 A1 | 8/2015 |
| WO | WO 2015/131428 A1 | 9/2015 |
| WO | WO 2016/112542 A1 | 7/2016 |
| WO | WO 2017/045897 A1 | 3/2017 |
| WO | WO 2017/202594 A1 | 11/2017 |
| WO | WO 2018/047092 A1 | 3/2018 |
| WO | WO 2018/069849 A1 | 4/2018 |
| WO | WO 2018/158081 A1 | 9/2018 |
| WO | WO 2018/184861 A1 | 10/2018 |
| WO | WO 2019/115996 A1 | 6/2019 |

OTHER PUBLICATIONS

International Search Report and Written Opinion dated Jan. 23, 2020 in PCT/EP2019/082777 filed on Nov. 27, 2019.
Russian Office Action dated Jul. 18, 2023, in corresponding Russian Patent Application No. 2021111754/03(025172) (with English Translation), 17 pages.
Extended European Search Report dated May 17, 2019 in corresponding European Patent Application No. 18208667.8, 11 pages.
Chinese Office Action and Search Report dated Oct. 27, 2023 issued in Chinese Patent Application No. 201980074130.0 filed Nov. 27, 2019, with English Translation, total 23 pages.
Japanese Office Action dated Nov. 30, 2023 issued in Japanese Patent Application No. 2021-524046 filed Nov. 27, 2019, with English Translation, total 6 pages.

\* cited by examiner

SENSOR FOR DEVICE AEROSOL-GENERATING SYSTEM

The disclosure relates to aerosol-generating electronic systems that operate by heating an aerosol-forming substrate. In particular, the disclosure relates to systems and devices using consumables filled with a liquid composition comprising an aerosol-forming substrate and to the consumable itself. More particularly, this disclosure relates to determining the fill level of the liquid composition in the consumable.

A liquid composition comprising an aerosol-forming substrate may be referred to as an e-liquid. In many e-liquid aerosol-generating systems, the e-liquid is stored in a cartridge received in an aerosol-generating device to heat the e-liquid to form an aerosol for inhalation by a consumer. When the cartridge is received by the aerosol-generating device, the e-liquid is typically not visible to the consumer. Because the consumer cannot see the e-liquid level, the consumer may not know when the e-liquid is nearly depleted. As such, the e-liquid may be depleted at a time when the consumer does not have a supply of e-liquid readily available to replenish the e-liquid in the cartridge or does not have a replacement cartridge available. Accordingly, the consumer may be unexpectedly deprived of use of the aerosol-generating system. In addition, when the cartridge is depleted or nearly depleted, excess heating of the remaining e-liquid may occur and may result in generation of undesired compounds. For at least these reasons, it may be desirable for a consumer to know the fill status of the e-liquid within the cartridge.

Monitoring fill status of a cartridge that is received by an aerosol-generating device presents challenges. For example, the cartridge is separate from the aerosol-generating device and often has no electrical power supply. In addition, the position of the cartridge and aerosol-generating device may vary, causing the liquid in the cartridge to move. Such movement may make static measurement challenging and may present obstacles to measurements taken in preferred orientations. Further, the volume of liquid in the cartridge is often quite small and may require accurate sensors. In addition, placing sensors in contact with the e-liquid may result in undesired interaction between the e-liquid and the sensors. For example, the e-liquid may be contaminated by materials in the sensor, the sensor may be degraded by the e-liquid, and the sensor may need to be sealed and complications may occur with the seal. Such factors may result in a higher cost consumable.

It would be desirable to provide an aerosol-generating e-liquid system that is capable of determining the fill level of e-liquid in the cartridge.

An aerosol-generating system may comprise a cartridge, an aerosol-generating device configured to receive the cartridge, a light source, and a detector. The cartridge may comprise a storage compartment configured to contain a liquid composition comprising an aerosol-forming substrate. The aerosol-generating device may comprise a power supply and control electronics operably coupled to the power supply. The light source may be operably coupled to the control electronics and positioned and oriented to emit light into the storage compartment of the cartridge. The light emitted from the light source may be absorbed by the liquid composition. The detector may be operably coupled to the control electronics and positioned and oriented to detect light emitted from the light source.

In some aspects, the invention includes an aerosol-generating system comprising a cartridge, an aerosol-generating device configured to receive the cartridge, a light source, and a detector. The cartridge comprises a storage compartment configured to contain a liquid composition comprising an aerosol-forming substrate. The aerosol-generating device comprises a power supply and control electronics operably coupled to the power supply. The light source is operably coupled to the control electronics and positioned and oriented to emit light into the storage compartment of the cartridge. The light emitted from the light source is absorbed by the liquid composition. The detector is operably coupled to the control electronics and positioned and oriented to detect light emitted from the light source. The light source and the detector are both configured to be located adjacent to a same side of the storage compartment and a surface of the storage compartment opposite the light source is configured to absorb light emitted into the storage compartment from the light source.

The control electronics may be configured to determine a fill level of the liquid composition in the storage compartment of the cartridge or may be configured to transmit data regarding a signal detected by the detector to another device for determining the fill level of the liquid composition in the storage compartment.

In some aspects, the invention may include an aerosol generating device that may comprise a power supply, control electronics operably coupled to the power supply, and a receptacle configured to receive a cartridge having a storage compartment containing a liquid composition comprising an aerosol-forming substrate. The device may also include a light source and a detector. The light source may be operably coupled to the control electronics and positioned and oriented to emit light into the storage compartment of the container. The detector may be operably coupled to the control electronics and positioned and oriented to detect the light emitted from the light source after the light has entered the storage compartment.

In some aspects, the invention includes an aerosol generating device comprising a power supply, control electronics operably coupled to the power supply, and a receptacle configured to receive a cartridge having a storage compartment containing a liquid composition comprising an aerosol-forming substrate. The device also includes a light source and a detector. The light source is operably coupled to the control electronics and positioned and oriented to emit light into the storage compartment of the container (or cartridge). The detector is operably coupled to the control electronics and positioned and oriented to detect the light emitted from the light source after the light has entered the storage compartment. The light source and the detector are both configured to be located adjacent to a same side of a storage compartment of a cartridge when a cartridge is received within the receptacle and a surface of the storage compartment opposite the light source is configured to absorb light emitted into the storage compartment from the light source.

The invention may include a cartridge for use in an aerosol generating device. The cartridge may comprise a storage compartment for housing a liquid composition that may comprise an aerosol-forming substrate, a light source, a first contact, a detector, and a second contact. The light source may be positioned and oriented to emit light into the storage compartment. The first contact may be operably coupled to the light source. The first contact may be positioned and oriented for electrical connection to a corresponding first contact of an aerosol-generating device when the cartridge is received in the aerosol-generating device. The detector may be positioned and oriented to detect the light emitter from the light source. The second contact may be operably coupled to the detector. The second contact may be positioned and oriented for electrical connection to a corresponding second contact of the aerosol-generating device when the cartridge is received in the aerosol-generating device.

In some aspects, the invention includes a cartridge for use in an aerosol generating device. The cartridge comprises a storage compartment for housing a liquid composition comprising an aerosol-forming substrate, a light source, a first contact, a detector, and a second contact. The light source is positioned and oriented to emit light into the storage compartment. The first contact is operably coupled to the light source. The first contact is positioned and oriented for electrical connection to a corresponding first contact of an aerosol-generating device when the cartridge is received in the aerosol-generating device. The detector is positioned and oriented to detect the light emitter from the light source. The second contact is operably coupled to the detector. The second contact is positioned and oriented for electrical connection to a corresponding second contact of the aerosol-generating device when the cartridge is received in the aerosol-generating device. The light source and the detector are both configured to be located adjacent to a same side of the storage compartment and a surface of the storage compartment opposite the light source is configured to absorb light emitted into the storage compartment from the light source.

Various aspects or embodiments of the systems, devices and cartridges containing liquid aerosol-forming substrates described herein may provide one or more advantages relative to currently available or previously described systems, devices, and cartridges for aerosol generating devices. For example, the systems, devices, and cartridges of the invention allow a consumer to be notified of the fill status of the liquid composition in the cartridge even if the liquid cannot be seen. This allows the consumer to anticipate the need to refill or replace the cartridge and allows the consumer to refill or replace the cartridge at an appropriate time when a supply of liquid composition or a replacement cartridge is readily available. In addition, the system may warn the consumer that the cartridge is depleted or nearly depleted so that the consumer may stop using the system until a replacement cartridge is inserted or until the liquid supply in cartridge is replenished, which may serve to prevent the consumer from being exposed to undesired compounds that may be associated with excessive heating of the liquid composition. In addition or alternatively, the system may be configured to reduce the temperature of the heater to avoid excessive heating that may result as the supply of the liquid composition is depleted. These and other advantages will be readily apparent to those of skill in the art upon reading the disclosure presented herein.

The sensing apparatus and methods described herein may be employed with any suitable aerosol-generating system that generates an aerosol from a liquid composition comprising an aerosol-forming substrate. The term "aerosol-generating" article, device, or system refers to an article, device, or system capable of releasing volatile compounds from an aerosol-forming substrate to form an aerosol that may be inhaled by a user. The term "aerosol-forming substrate" refers to a substrate capable of releasing volatile compounds, which may form an aerosol. Typically, the substrate is heated to cause the release of the volatile compounds. A liquid aerosol-forming substrate is a substrate that is liquid at ambient temperature, for example, at about 15° C. to about 30° C. Liquid aerosol-forming substrates are considered to include liquid solutions, suspensions, dispersions, and the like. Preferably, the liquid aerosol-forming substrate is a solution.

Preferably, the aerosol-generating system is a handheld system having a mouthpiece for insertion in the mouth of a consumer. The aerosol-generating system includes a cartridge comprising a storage compartment configured to contain a liquid composition comprising an aerosol-forming substrate and comprises an aerosol-generating device configured to receive the cartridge. The aerosol-generating device or the cartridge may comprise the mouthpiece. Preferably, the cartridge comprises the mouthpiece.

The aerosol-generating device comprises a power supply and control electronics operably coupled to the power supply. The power supply and control electronics are operably coupled to an aerosol-generating element, which when activated is configured to generate an aerosol from the liquid composition comprising the aerosol-forming substrate. Preferably, the aerosol-generating element comprises a heating element. Preferably, the heating element comprises an electrically resistive heating element. Preferably, the heating element comprises a liquid permeable heating element, such as a porous electrically resistive material. Preferably, the heating element comprises a mesh of electrically resistive filaments. The mesh may be substantially planar or may comprise a substantially planar portion.

The cartridge or the device may comprise the aerosol-generating element. If the cartridge comprises the aerosol-generating element, the aerosol-generating element is electrically coupled to the power supply and control electronics when the cartridge is received by the aerosol-generating device. If the aerosol-generating device comprises the aerosol-generating element, the aerosol-generating element is electrically coupled to the power supply and control electronics and is positioned to cause the liquid composition to form an aerosol when the cartridge is received by the aerosol-generating device and the aerosol-generating element is activated. The device is considered to comprise the aerosol-generating element when the aerosol-generating element may be removably attachable to the aerosol-generating device.

The aerosol-generating system defines an airflow path that causes aerosol formed from the liquid composition, when the aerosol-generating element is activated, to be entrained in air that flows through the path for inhalation by a consumer when the consumer draws on the mouth end of the system.

The cartridge may include a retention material that is capable of absorbing, storing, or absorbing and storing the liquid composition comprising the aerosol-forming substrate. The retention material is in contact with the liquid composition comprising the aerosol-forming substrate and may be in contact with the aerosol-generating element, which may be a part of the cartridge or the aerosol-generating device.

The retention material may include a capillary material having a fibrous or porous structure which forms a plurality of small bores or micro-channels. Liquid aerosol-forming substrate may be transported through the capillary material by capillary action. The retention material may include a plurality of fibers, threads, or other fine bore tubes that form a bundle of capillaries. The fibers or threads may be generally aligned to convey the liquid composition comprising the aerosol-forming substrate from one surface of the retention material to a generally opposing surface of the retention material. Alternatively, the retention material may include sponge-like or foam-like material. The retention material may include any suitable material or combination of materials. Examples of suitable materials include a sponge or foam material, ceramic- or graphite-based materials in the form of fibers or sintered powders, foamed metal or plastic materials, fibrous materials (for example, spun or extruded fibers, such as cellulose acetate, polyester, bonded polyolefin, polyethylene, polypropylene fibers, nylon fibers, ceramic fibers), and combinations thereof. In one exemplary embodiment, the retention material includes high density polyethylene (HDPE) or polyethylene terephthalate (PET).

The cartridge may include a retention material and a transport material. The transport material is a material that actively conveys liquid from one end of the material to another, for example by capillary action, such as a wick. The retention material may be in contact with the liquid composition comprising the aerosol-forming substrate and in contact with the transport material. The transport material may transport the liquid composition from the retention material to the aerosol-generating element.

The transport material may have a first surface facing the high retention material and an opposing second surface facing the aerosol-generating element. The shape of at least a portion of the surface of the transport material may conform to a shape of a surface of the aerosol-generating element with which the second surface of the transport element may contact.

The transport material may have a fibrous or porous structure. The transport material preferably comprises a bundle of capillaries. For example, the transport material may comprise a plurality of fibers or threads or other fine bore tubes. The transport material may be configured to primarily transport liquid in a direction orthogonal or normal to the thickness direction of the transport material. The transport material may preferably comprise elongate fibers such that capillary action occurs in the small spaces or micro-channels between the fibers.

The transport material may be made of a heat resistant material having a thermal decomposition temperature of at least 160° C. or higher, such as approximately 250° C. or higher. The transport material may comprise fibers or threads of cotton or treated cotton, such as acetylated cotton. Other suitable materials could also be used, such as, for example, ceramic- or graphite based fibrous materials or materials made from spun, drawn, or extruded fibers, such as fiberglass, cellulose acetate, or any suitable heat resistant polymer. The fibers of the transport material may each have a thickness of between 10 μm and 40 μm and more particularly between 15 μm and 30 μm. The transport material may have any suitable capillarity and porosity so as to be used with liquid having different physical properties. The transport material may transport the liquid composition comprising the aerosol-forming substrate by capillary action. The liquid composition comprising aerosol-forming substrate may have physical properties including viscosity, surface tension, density, thermal conductivity, boiling point, vapor pressure, and the like, that are tailored to facilitate transport of the liquid composition comprising the aerosol-forming substrate through the transport material by capillary action.

The retention material or the retention material and the transport material, if present, may be disposed in the storage compartment of the cartridge or may be external to the storage compartment, provided that the retention material, if present, is positioned to contact the liquid composition comprising the aerosol-forming substrate disposed in the storage compartment. For example, a liquid permeable wall or a liquid permeable portion of a wall may have an internal surface that forms at least a portion of the storage compartment and may have an outer surface with which the retention material is in contact.

The aerosol-generating system includes sensing apparatus for detecting the volume of the liquid composition in the storage compartment or for detecting the fill level of the liquid composition in the storage compartment. The sensing apparatus includes a light source and a light detector. The light source and the detector are operably coupled to the control electronics and power supply of the aerosol-generating device. The light source is positioned and oriented to emit light into the storage compartment of the cartridge. The detector is positioned and oriented to detect light emitted from the light source. The cartridge or the aerosol-generating device may comprise the light source. The cartridge or the aerosol-generating device may comprise the detector.

If the cartridge comprises the light source, the light source is preferably operably coupled to the power supply and the control electronics of the aerosol-generating device when the cartridge is received by the device. For example, the cartridge may comprise an external electrical contact that is electrically coupled to the light source. The aerosol-generating device may comprise a corresponding contact that is operably coupled to the control electronics and power supply. When the cartridge is received by the device, the external contact of the cartridge may contact the corresponding contact of the device to operably couple the light source to the control electronics and power supply of the device. The cartridge and the device may have corresponding features to ensure proper orientation to achieve contact between the electrical contacts when the cartridge is received by the device.

If the cartridge comprises the light source, the light source may be exposed to an interior of the storage compartment or may be sealed relative to the interior of the storage compartment. For example, the cartridge may comprise a window of material through which light from the light source may be transmitted to the interior of the storage compartment.

If the device comprises the light source, the cartridge comprises a window of material through which light from the light source may be transmitted to the interior of the storage compartment when the cartridge is received by the device. The cartridge and the device may have corresponding features to ensure proper alignment of the light source and the window when the cartridge is received by the device.

If the cartridge comprises the detector, the detector is preferably operably coupled to the power supply and the control electronics of the aerosol-generating device when the cartridge is received by the device. For example, the cartridge may comprise an external electrical contact that is electrically coupled to the detector. The aerosol-generating device may comprise a corresponding contact that is operably coupled to the control electronics and power supply. When the cartridge is received by the device, the external contact of the cartridge may contact the corresponding contact of the device to operably couple the detector to the control electronics and power supply of the device. The cartridge and the device may have corresponding features to ensure proper orientation to achieve contact between the electrical contacts when the cartridge is received by the device.

If the cartridge comprises the detector, the detector may be exposed to an interior of the storage compartment or may be sealed relative to the interior of the storage compartment. For example, the cartridge may comprise a window of material through which the light from inside the storage compartment may be transmitted to the detector located external to the storage compartment and adjacent to the window.

If the device comprises the detector, the cartridge comprises a window of material through which the light from inside the storage compartment may be transmitted to the detector when the cartridge is received by the device. The cartridge and the device may have corresponding features to ensure proper alignment of the detector and the window when the cartridge is received by the device.

The light source may emit light having a wavelength that is absorbed by the liquid composition comprising the aerosol-forming substrate. For example, the light source may emit light having a wavelength in a range from about 10 nm to about 1 mm. Preferably, the light source emits infrared light. For example, the light source may emit light having a wavelength in a range from about 100 nm to about 1 mm. For example, the light source may emit light having a wavelength from about 200 nm to about 25 micrometers or having a wavelength from about 500 nm to about 10 micrometers or from about 700 nm to about 4 micrometers.

Any suitable light source may be employed. For example, the light source may be relatively monochromatic or may emit light having a wavelength within a range. Preferably, the range of the wavelength over which the light is emitted is narrow.

In some embodiments, a filter may be employed to restrict the wavelength of light that may pass through the filter. The filter may be, for example, an optical bandpass filter, which allows light within a certain band of wavelengths to pass and restricts passage of light of wavelengths outside the band to pass. The filter may be positioned between the light source and the interior of the storage compartment. When such a filter is employed, the light source may emit a broad spectrum of light.

The light that passes from the light source through the liquid composition in the storage chamber of the cartridge may be omnidirectional, directional, or focused. Light may be focused in any suitable manner, such as by employing a lens to focus light to a particular point. Light may be made directional by employing a directional source, such as a light emitting diode, a laser diode, or a collimator. In some embodiments, light may be focused and collimated or focused and directional. It will be understood that the use of omnidirectional, directional, or focused light may depend on the detection scheme employed. Some examples of detection schemes that may be employed are discussed below in more detail.

The light source, or filter, may be selected based on wavelengths of light that will be absorbed by the liquid composition comprising the aerosol-forming substrate. In addition or alternatively, a compound that absorbs light emitted by the light source may be added to the liquid composition to ensure that the liquid composition absorbs the emitted light.

Any suitable liquid composition comprising an aerosol-forming substrate may be used with the systems described herein. Suitable aerosol-forming substrates may include plant-based material. For example, an aerosol-forming substrate may include tobacco or a tobacco-containing material containing volatile tobacco flavor compounds, which are released from the aerosol-forming substrate upon heating. In addition or alternatively, an aerosol-forming substrate may include a non-tobacco containing material. An aerosol-forming substrate may include homogenized plant-based material. An aerosol-forming substrate may include at least one aerosol former. Examples of aerosol formers include polyhydric alcohols, such as triethylene glycol, 1,3-butanediol, propylene glycol, and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. An aerosol-forming substrate may include other additives and ingredients such as flavorants. Preferably an aerosol-forming substrate includes nicotine. Preferably, the aerosol-forming substrate is a liquid aerosol-forming substrate. In some embodiments, an aerosol-forming substrate includes glycerol, propylene glycol, water, nicotine and, optionally, one or more flavorants.

Any suitable detector may be used. For example, the detector may be a photodetector, such as a photodiode. The detector is configured to detect a wavelength of light emitted by the light source or passed through a filter, if employed. Preferably, the light source and filter, if present, emits and passes through infrared light, and the detector absorbs infrared light. For example, the detector may detect light having a wavelength in a range from about 100 nm to about 1 mm. For example, the detector may detect light having a wavelength from about 200 nm to about 25 micrometers or having a wavelength from about 500 nm to about 10 micrometers or from about 700 nm to about 4 micrometers. In some embodiments, the detector is capable of detecting light over a broad spectrum of wavelengths, but the wavelength of light that reaches the detector is limited by the light source and filter, if present.

The cartridge may comprise a light guide to direct light that has travelled through the liquid composition to the detector. For example, the cartridge may comprise a collimator, a mirror or another reflective surface, a lens, or the like for directing light to the detector. It will be understood that the apparatus to direct light to the detector may depend on the detection scheme employed. Some examples of detection schemes that may be employed are discussed below in more detail.

Because the liquid composition absorbs light emitted by the light source, the amount of light that reaches the detector may be reduced relative to the amount of light transmitted by the light source. The reduction in the light detected by the light source will be proportional to the volume of the liquid composition in the storage compartment of the cartridge.

For the liquid composition comprising the aerosol-forming substrate, which may be considered to contain known or relatively unchanging concentrations of compounds, the absorbance of light by the liquid composition should be proportional to the path length of the light in the through the liquid composition in the storage tank. Accordingly, if more liquid composition is present in the storage compartment, then more light should be absorbed and less should reach the detector.

The detector may be positioned and oriented relative to the light source to detect light that reflects off a liquid-air interface within the storage compartment of the cartridge. In such orientations, the light may pass from the light source through the liquid composition to a liquid-air interface and back through the liquid composition to the detector. This may extend the length of the path that the light travels to reach the detector, and thus may increase the sensitivity of the system. In some embodiments, the detector is positioned and oriented relative to the light source to detect light that passes through the liquid composition and through the liquid-air interface.

The detector may be positioned and oriented in any suitable manner relative to the light source, provided that light emitted by the light source may reach the detector. The detector may be located adjacent to an opposing side of the storage compartment relative to the light source or may be located adjacent to the same side as the light source. If a reflected signal is detected by the detector, the light source and the detector may be adjacent to the same side. The detector may be positioned at or on the same side of the storage compartment as the light source. Both the light source and the detector may be positioned at or on a same side of the storage compartment. Both the light source and the detector may be positioned in vicinity of a same side of the storage compartment.

The storage compartment has a length extending from a bottom of the storage compartment to a top of the storage compartment. The "bottom" of the storage compartment may be the surface of the storage compartment that is the furthest from the mouth end of the system. The light source may be located adjacent to the top or bottom of the storage compartment and the detector may be located adjacent to the top or bottom of the storage compartment. When the light source and the detector are adjacent to opposing top and bottom sides of the storage compartment, the cartridge preferably comprises a light guide to direct light to the detector.

The storage compartment comprises a peripheral sidewall that extends from the bottom to the top of the storage compartment. When the light source and the detector are adjacent to opposing top and bottom sides of the storage compartment, the interior surface of the sidewall preferably reflects the light emitted from the light source or passed through the filter, if present.

The light source and the detector may be adjacent to the sidewall of the storage compartment between the top and bottom of the storage compartment.

The system may comprise a plurality of light sources and a plurality of detectors, each of which are operably coupled to, when on the device, or operably couplable to, when on the cartridge, the power supply and control electronics of the aerosol-generating device. The position and orientation of the plurality of light sources and detectors may be varied. In some embodiments, the light sources are positioned and oriented adjacent to one surface, such as a top or bottom surface, and the detectors are positioned and oriented adjacent to the same surface or an opposing surface. In some embodiments, the light sources and the detectors are positioned about a periphery of the storage chamber, such as about the sidewall. The position of the light sources and the detectors about the periphery may be alternated.

The interior surface of the storage compartment of the cartridge may reflect or absorb light emitted from the light source or passed through the filter, if present. The interior surface of the storage compartment preferably reflects the light if the total light detection or near total light detection is intended to be achieved. When total light detection or near total light detection is intended, the light source or light sources may be omnidirectional. When total light detection or near total light detection is intended, the system may include a plurality of detectors. In addition or alternatively, the system may include a light guide to direct light to a detector or detectors.

If the light source and detector are located adjacent to the same side of the storage compartment and are configured to detect absorbance by the liquid composition by reflection, the surface of the storage compartment opposite the light source preferably absorbs light emitted from the light source or passed through the filter, if present. The signal received by the detector when the liquid composition fills the storage compartment may be relatively low, may increase as the liquid composition is depleted, and may reach essentially zero when the storage compartment is empty because the light may be absorbed by the opposing surface and thus may not be reflected back to the detector. The light source and the detector may be located adjacent to the same side of the storage compartment when the cartridge is received in the aerosol-generating device.

It may be desirable for the device and cartridge received by the device to be in a particular orientation when the light source and detector are activated for determining the volume of the liquid composition in the storage chamber. To aid in determining the orientation of the device and cartridge received in the device, the device may comprise an inertial sensor operably coupled to the power supply and control electronics. Any suitable inertial sensor may be employed. For example, the inertial sensor may comprise an accelerometer, a gyroscope, or an accelerometer and gyroscope. Preferably, the inertial sensor comprises a 1-axis accelerometer, which axis is along the longitudinal axis of the storage compartment. Such an accelerometer may be use as an inclinometer as it measures the value of acceleration due to gravity. When the accelerometer measures a value of 1 g along its axis, the storage compartment should be oriented in a vertical position with the bottom down. Such orientations may be preferred when the light source and detector are adjacent to the top or bottom surfaces of the storage tank.

Input from the inertial sensor may be used in determining the tilt angle of the device, which may be used in determining the volume of the liquid composition in the storage compartment based on tilt angle, may be used to determine which pair of light sources and detectors to activate, or the like.

The device may comprise a display or may be configured to transmit information to another device, such as a computer or mobile smart phone, for display. The display may alert a consumer to orient the device in a particular orientation prior to determining the volume or fill level of the liquid composition in the storage compartment. For example, the display may instruct the consumer to place the device in a vertical, bottom-down orientation or may instruct the consumer to place the device in a base configured to orient the device in a vertical, bottom-down orientation. If the device comprises an inertial sensor, the light source and detector may be activated once the device is properly oriented. In addition or alternatively, the device may comprise an input operably coupled to the control electronics that allows the user to indicate that the device is properly oriented and that volume or fill level sensing may commence.

In some preferred embodiments, the system includes a single light source and a single detector adjacent to the bottom of the storage compartment. The device or the cartridge may comprise the light source and the detector. The device and storage compartment received by the device are preferably oriented in a vertical, bottom-down orientation when the light source and detector are activated to measure the volume or fill level of the liquid composition in the storage tank. Preferably, the light source, the detector, and a liquid-air interface of the liquid composition in the storage compartment, which may reflect light from the light source to the detector, are oriented in a triangular relationship. The device preferably comprises an inertial sensor or is capable of alerting a consumer to place the device in a vertical, bottom-down orientation. Once a vertical, bottom-down orientation is detected or indicated, the light source and detector may be activated. The amount of light received by the detector may be used by the control electronics to determine the volume of liquid in the storage compartment or the fill level of the storage compartment. The top internal surface of the storage compartment preferably absorbs the light emitted from the storage compartment. For example, the top internal surface may be black.

The signal received by the detector when the liquid composition fills the storage compartment may be relatively low due to absorption of the light by the liquid composition, may increase as the liquid composition is depleted, and may reach essentially zero when the storage compartment is empty because the light may be absorbed by the opposing surface and thus may not be reflected back to the detector.

In some cases when a small volume of liquid composition remains in the storage compartment, the signal emitted from the light source may not reach the detector due to the angle of reflection being too great. In such cases, the signal detected by the detector may be similar to the signal of an empty storage compartment. That is, the signal may reach essentially zero. The system may initiate a complementary process in such cases to verify whether the storage compartment is empty or whether a small volume of the liquid composition remains in the storage compartment. The complementary process includes providing instructions to the consumer to invert the device to a vertical, bottom-up orientation, which will cause any remaining liquid to be located at the top of the storage compartment, which will be oriented on the bottom. The light source and detector may be activated. If a small volume of the liquid composition is in the storage compartment, some of the light will reflect off the air-liquid interface and return to the detector, which will receive a signal. If no liquid composition remains in the storage compartment, the light will be absorbed by the top of the storage compartment, and essentially no signal will be detected by the detection. Thus, if a signal is detected by the complementary process, a determination may be made that a small volume of liquid composition remains in the storage compartment, and if no signal is detected by the complementary process, a determination may be made that no liquid composition remains in the storage compartment.

In some preferred embodiments, the system comprises a plurality of light sources and detectors are positioned about a periphery of the storage compartment in an alternating manner. For example, if the storage compartment is cylindrical, the light sources and detectors may form a ring around the periphery of the storage compartment. Multiple rings of alternating light sources and detectors may be disposed about the periphery of the storage compartment. The detection scheme is preferably based on reflection of the light from the light source off a liquid-air interface to a detector. The light sources may be sequentially activated while light received by the detectors is measured to identify a light source and at least one detector that are oriented such that the light passes through the liquid composition prior to reaching the detector. If the light does not pass through the liquid composition, the amount of light reaching the detector will be greater than the amount of light that reaches the detector when the light passes through the liquid composition due to absorbance of the light by the liquid composition. One or more detected signals indicative of light passing through the liquid composition may be used to determine the volume of the liquid composition in the storage compartment or the fill level of the liquid composition in the storage compartment.

In some preferred embodiments, the system includes a light source adjacent to a bottom or top of the storage compartment and a detector adjacent to the bottom of the storage compartment, where the light source and the detector are adjacent to opposing surfaces. The device preferably comprises an inertial sensor or is capable of alerting a consumer to place the device in a vertical, bottom-down orientation. Once a vertical, bottom-down orientation is detected or indicated, the light source and detector may be activated. The amount of light received by the detector may be used by the control electronics to determine the volume of liquid in the storage compartment or the fill level of the storage compartment. The aerosol generating element may be positioned along and exterior to sidewall of the storage compartment in such configurations so that the aerosol-generating element does not interfere with the transmission of the light through the storage compartment from the top to the bottom or bottom to top. The aerosol-generating element may form a portion of the sidewall of the storage compartment. The aerosol-generating element and the portion of the sidewall along which the aerosol-generating element is position is preferably permeably to the liquid composition in the storage compartment. For example, the aerosol-generating element may be porous. Preferably, the aerosol-generating element comprises a heating element. The cartridge may comprise a channel between the aerosol-generating element and a wall of the cartridge that may form a portion of the airflow path for delivering aerosol to the consumer for inhalation.

In some preferred embodiments, the system includes a light source adjacent to a bottom or top of the storage compartment and a detector adjacent to the bottom of the storage compartment, where the light source and the detector are adjacent to opposing surfaces. The system may comprise multiple light sources on one side and multiple detectors on the other side. Preferably, the internal surface of the storage compartment reflects light emitted by the light source or light sources. The cartridge may comprise a light guide to direct the light to the detector or detectors. In addition or alternatively, the light source or light sources may be omni-directional. The aerosol generating element may be positioned along and exterior to sidewall of the storage compartment in such configurations so that the aerosol-generating element does not interfere with the transmission of the light through the storage compartment from the top to the bottom or bottom to top. The aerosol-generating element may form a portion of the sidewall of the storage compartment. The aerosol-generating element and the portion of the sidewall along which the aerosol-generating element is position is preferably permeably to the liquid composition in the storage compartment. For example, the aerosol-generating element may be porous. Preferably, the aerosol-generating element comprises a heating element. The cartridge may comprise a channel between the aerosol-generating element and a wall of the cartridge that may form a portion of the airflow path for delivering aerosol to the consumer for inhalation.

In some preferred embodiments, the system includes a light source and a detector adjacent to the bottom of the storage compartment. The device or the cartridge may comprise the light source and the detector. The system may comprise a plurality of light sources and a plurality of detectors adjacent to the bottom of the storage compartment. The device may comprise an inertial sensor or may be capable of alerting a consumer to place the device in a vertical, bottom-down orientation. Once a vertical, bottom-down orientation is detected or indicated, the light source and detector may be activated. The top internal surface of the storage compartment preferably absorbs the light emitted from the storage compartment. The control electronics may be configured to activate all the light sources at the same time and may be configured to receive input from all the detectors at the same time.

Regardless of the manner in which light is emitted and detected, the signal detected by the detector may be evaluated based on the laws of absorption, calibration using known volumes of liquid composition having known components of known concentration, or based on the laws of absorption and calibration using known volumes of liquid composition having known components of known concentration. The control electronics may comprise memory in which a conversion table correlating signal received to liquid composition level. In addition or alternatively, the control electronics may comprise a transmitter to provide information regarding detected signal or signals to an external device, such as a computer or mobile smartphone, for determining the liquid fill level.

The control electronics of the aerosol-generating device may be provided in any suitable form and may, for example, include a controller or a memory and a controller. The controller may include one or more of an Application Specific Integrated Circuit (ASIC) state machine, a digital signal processor, a gate array, a microprocessor, or equivalent discrete or integrated logic circuitry. Control electronics may include memory that contains instructions that cause one or more components of the circuitry to carry out a function or aspect of the control electronics. Functions attributable to control electronics in this disclosure may be embodied as one or more of software, firmware, and hardware.

Reference will now be made to the drawings, which depict one or more aspects described in this disclosure. However, it will be understood that other aspects not depicted in the drawings fall within the scope and spirit of this disclosure. Like numbers used in the figures refer to like components, steps and the like. However, it will be understood that the use of a number to refer to a component in a given figure is not intended to limit the component in another figure labeled with the same number. In addition, the use of different numbers to refer to components in different figures is not intended to indicate that the different numbered components cannot be the same or similar to other numbered components. The figures are presented for purposes of illustration and not limitation. Schematic drawings presented in the figures are not necessarily to scale.

Figure 1:
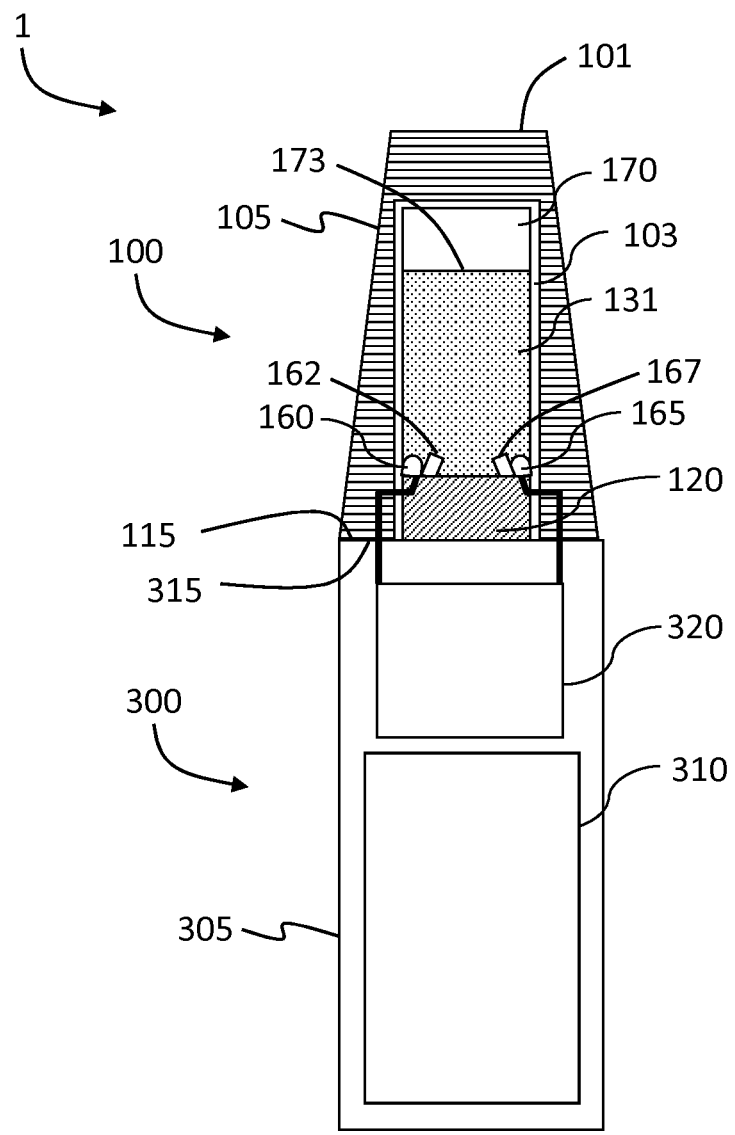
FIG. 1 is a schematic drawing of an example of an aerosol-generating system.

Referring now to FIG. 1, an aerosol-generating system 1 includes two main components, a cartridge 100 and an aerosol-generating device 300. The cartridge 100 extends from a mouth end 101 to a connection end 115. The cartridge 100 is removably connected to a corresponding connection end 315 of the aerosol-generating device 300. The aerosol-generating device 300 contains a housing 305 in which a power supply, such as a battery 310, and control electronics 320, and any associated electronic circuitry (for example, electrical conductors and contacts extending through the housing) are disposed. The aerosol-generating system 1 may be portable and may have a size comparable to a conventional smoking article, such as a cigar or cigarette.

The cartridge 100 includes a housing 105 containing an aerosol-generating element, which in this case comprises a heater assembly 120 comprising an electrically resistive heating element, and a storage compartment 103 in which a liquid composition comprising an aerosol-forming substrate 131 is held. When the cartridge 100 is received by the aerosol-generating device 300, such as when the cartridge 100 is connected to the aerosol-generating device 300 as depicted in FIG. 1, the heater element is operably coupled to the control electronics 320 and the power supply 310 so that the heater element may be activated to heat the liquid composition 131. The heater assembly 120 may comprise high retention material and transport material (not shown), where the high retention material is in contact with the liquid composition 131 and the transport material contacts the high retention material and the heating element.

An airflow passage (not show) extends through the cartridge 100 from an air inlet (not shown) formed on a side of the housing 105, past the heater assembly 120, and from the heater assembly 120 to a mouthpiece opening formed at the mouth end 101 of the housing 105.

The system is configured so that a user can puff or draw on the mouth end 101 of the cartridge 100 to draw aerosol from the system 1. When the system 1 is activated, the control electronics 320 controls the supply of electrical power from the battery 310 to the cartridge 100. The control electronics 320 may include an airflow sensor (not shown) and may supply electrical power to the heating element of the heater assembly 120 when a user puffs on the cartridge 100, as detected by the airflow sensor. Alternatively, the system 1 may be activated by pushing on a button or in another similar manner. When the system 1 is activated, the heating element of the heater assembly 120 is activated, thus heating the transport material, which wicks liquid aerosol-forming substrate 131 from the high retention material to the heater element. The heater element 120 heats the liquid aerosol-forming substrate 131 and generates a vapor that is entrained in the airflow passing through the airflow passage. The vapor cools within the airflow in passage to form an aerosol, which is then drawn into the user's mouth through the opening at the mouth end 101.

The cartridge 100 comprises a light source 160 and a light detector 165 extending into the storage compartment 103 adjacent to the bottom of the storage compartment 103. The light source 160 and the light detector 165 may be sealed relative to an interior of the cartridge 100. The light source 160 and the light detector 165 electrically couple to the control electronics 320 and the power supply 310 when the cartridge 100 is received by the device 300 through contacts (not shown). The control electronics 320 are configured to activate the light source 160, which is positioned an oriented to emit light into the storage compartment 130, and are configured to receive a signal from the detector 165, which is positioned and configured to detect light that is emitted from the light source 160 that reflects off the liquid-air interface 173 formed between the liquid composition 131 and air 170 in the storage compartment 103. The cartridge 100 comprises light blocking elements 162, 167 to prevent straight line transmission of light emitted from the light source 160 to the detector 167. The walls defining the storage compartment 130 or the housing 150 of the cartridge are opaque to light so that outside light does not interfere the light detection sensing system.

The storage compartment 103 is shaped such that an isosceles triangle is formed between the light source 160, the liquid-air interface 173, and the detector 165 when the device 300 is oriented such that the storage compartment 103 is positioned in a vertical, bottom-down orientation (as depicted in FIG. 1). In the embodiments depicted in FIG. 1, the interior surface of the storage compartment 103 preferably absorbs light emitted by the light source 160. For example, the interior surface of the storage compartment 103 may be black. However, if the interior surface of the storage compartment 103 reflects the emitted light, the sensing system would be expected to properly function.

Figure 2:
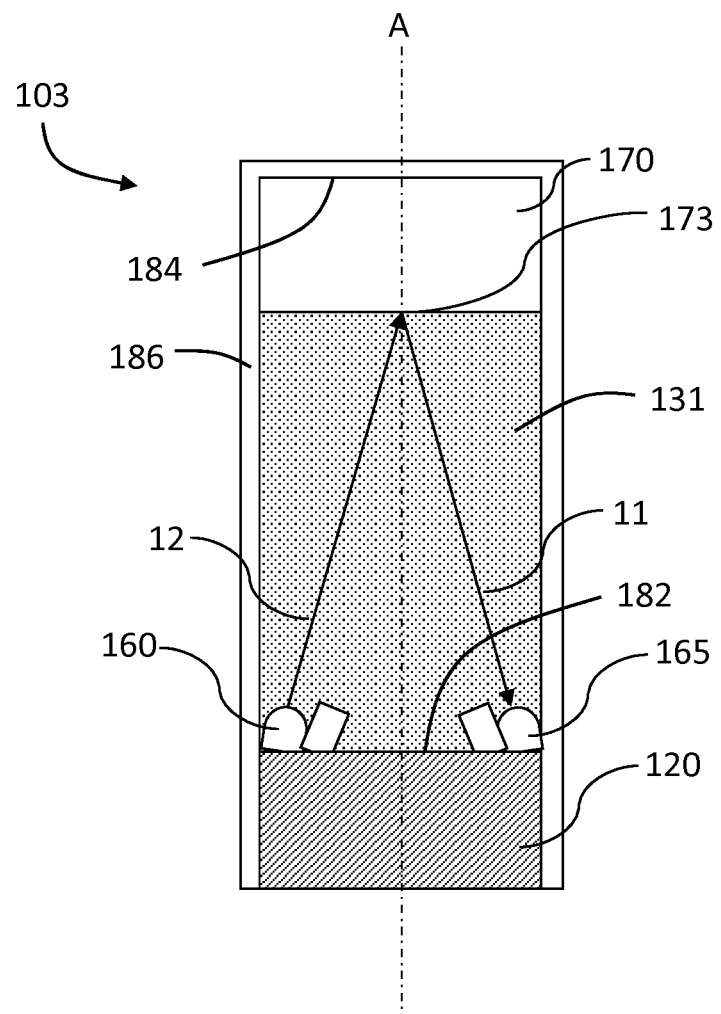
FIG. 2 is a schematic drawing of a close-up view of a storage compartment and heating assembly of an embodiment of a cartridge for use in an aerosol-generating system.
Figure 3:
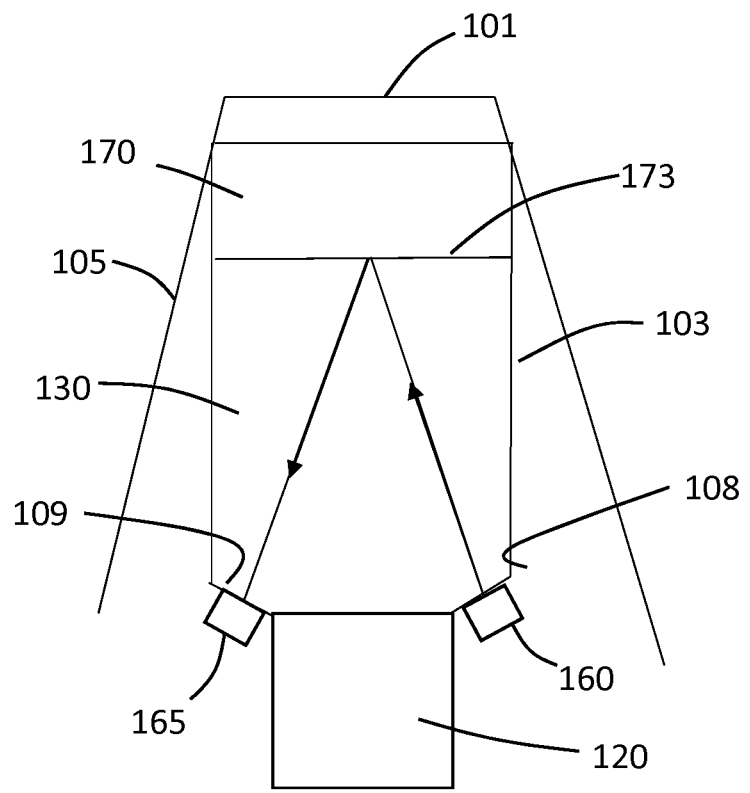
FIG. 3 is a schematic drawing of an example of a cartridge and a light source and detector of an aerosol-generating device.
Figure 4A:
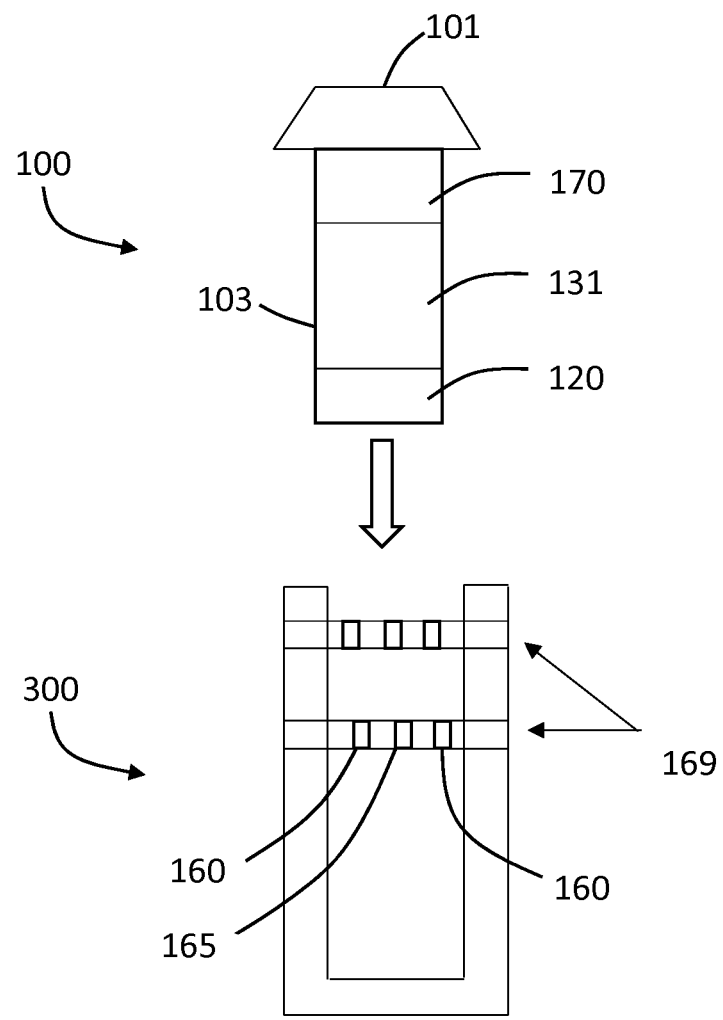
FIG. 4A is a schematic drawing of an example of cartridge and an aerosol-generating device configured to receive the cartridge.
Figure 4B:
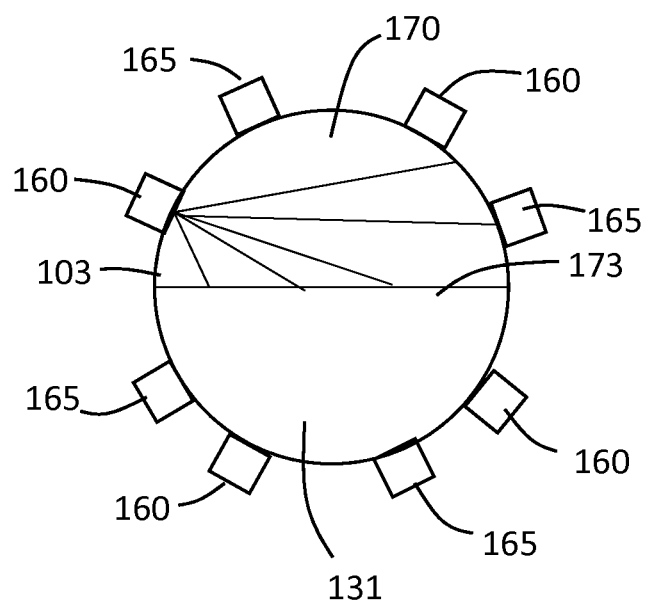
FIG. 4B is a schematic drawing illustrating a cross-section of the cartridge and light sources and detectors of the aerosol-generating device of FIG. 4A in a horizontal orientation.

FIG. 2 is a close-up view of the storage compartment 103 of a cartridge. The storage compartment 103 has a longitudinal axis A, bottom internal surface 182, a top internal surface 184, and a sidewall 186 extending from the bottom 182 to the top 184. A liquid composition 131 comprising an aerosol-generating substrate is held in the storage compartment 103 and is in communication with a heating assembly 120. A liquid-air interface 173 is formed between the liquid composition 131 and air 170 in the storage compartment 103.

The light source 160 and a light detector 165 extend into the storage compartment 103 adjacent to the bottom surface 182. As illustrated, light emitted from the light source 160 may reflect off the liquid-air interface 173 along the longitudinal axis A to be directed to the detector 165. The path of reflected light forms an isosceles triangle having the light source 160 and the detector 165 as the base and two sides 11, 12 of equal length. The path length that the light travels should be proportional to the light absorbed by the liquid composition 131 and the signal detected at the detector 165.

FIG. 3 depicts some components of an embodiment of a cartridge and a device. The cartridge comprises a housing 105 that forms a mouth end 101 and comprises a storage compartment 103. A liquid composition 131 comprising an aerosol-forming substrate is disposed in the storage compartment 130. A liquid-air interface 173 is formed between the liquid composition 131 and air 170 in the storage compartment 103. The storage compartment 103 includes a first window 108 and a second window 109 adjacent to the bottom. The first 108 and second 109 windows are transparent to light emitted from light source 165. The light source 165 and the detector 160 are part of the aerosol-generating device. When the cartridge is received by the device, the light source 165 is positioned and oriented to transmit light into the storage compartment 103 through the first window 108, and the detector 165 is positioned and oriented to detect the emitted light that passed through the second window 109. The detector 165 is positioned to detect light that reflects off the liquid-air interface 173.

The heater assembly 120 is below the bottom of the storage compartment 103. However, the heater assembly may be positioned at any other suitable location.

FIG. 4A illustrates a system that comprises a cartridge 100 and an aerosol-generating device 300 configured to receive the cartridge 100. The aerosol-generating device 300 comprises rings 169 of alternating light sources 160 and detectors 165 such that, when the cartridge 100 is received by the device 300, the rings 169 of alternating light sources 160 and detectors 165 circumscribe the periphery of the storage compartment 103 of the cartridge 100. The cartridge 100 includes a heater assembly 120 that operably couples with the power supply and control electronics of the device 300 when the cartridge 100 is received by the device 300. The cartridge 100 forms a mouth end 101 for insertion into the mouth of a consumer. A liquid composition 131 comprising an aerosol-forming substrate is disposed in the storage compartment 103. A liquid-air interface 173 is formed between the liquid composition 131 and air 170 in the storage compartment 103. Sidewalls, or portions thereof, are transparent to light emitted by the light sources 160 to allow light from the light sources 160 to enter the storage compartment 103 and to allow the emitted light to exit the storage compartment 103 to reach the detectors 165. The light sources are preferably omnidirectional.

In FIG. 4B, the device and cartridge are positioned horizontally such that a liquid-air interface 173 formed between the liquid composition 131 and air 170 in the storage compartment 103 extends parallel with the longitudinal axis of the storage compartment 103. In this configuration, some of the light sources 160 and detectors 165 are above the level of the liquid composition 131 and some are below the liquid composition 131. The light sources 160 may be sequentially activated while light is detected at the detectors 165 to identify at least one pair of a light source 160 and a detector 165 that are below the level of the liquid composition 131 based on the signal received at the detector. One or more of such pairs may be used to determine the fill level or volume of the liquid composition 131 in the storage compartment 103. It should be understood that the fill level or volume of liquid composition may also be detected when the device and cartridge are in different orientations using a similar process.

In FIG. 5, the cartridge 100 is received by the aerosol-generating device 300. The device 300 has a housing 305 that defines a cavity for receiving the cartridge 100. The cartridge 100 comprises a storage compartment 130 and a heater assembly 120. The heater assembly 120 is positioned along a sidewall of the storage compartment 103 so that the heater assembly 120 does not interfere with transmission of light through the storage compartment 103 from the bottom to the top of the storage compartment 103. A liquid composition 131 comprising an aerosol-forming substrate is disposed in the storage compartment 103 and a liquid-air interface 173 is formed between the liquid composition 131 and air 170 in the storage compartment 103.

A passageway 400 is formed between the heating element 120 and the housing 305 of the aerosol-generating device 300. The passageway 400 forms a part of an air flow path to carry aerosol to the consumer for inhalation.

The light 160 and detector 165 are positioned outside of the storage compartment 103. Accordingly, the storage compartment comprises transparent portions at the top and bottom to allow light emitted from the light source 160 to travel through the storage compartment 130 to reach the detector 165.

Figure 5:
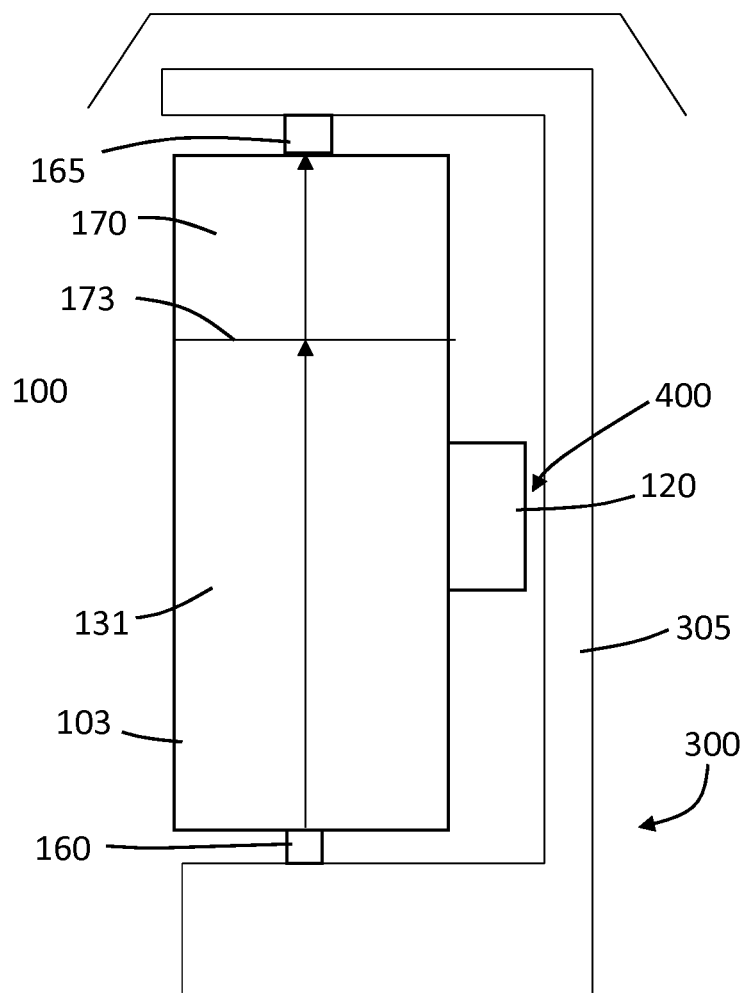
FIG. 5 is a schematic drawing illustrating a section of portions of an aerosol-generating device and a cartridge received by the device.
Figure 6:
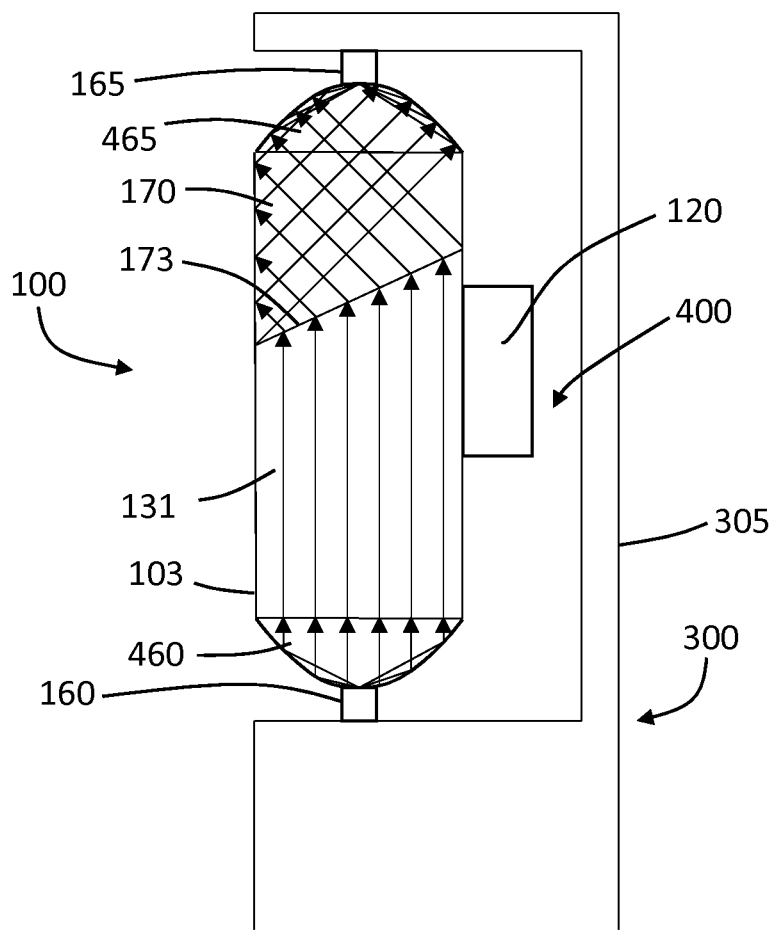
FIG. 6 is a schematic drawing illustrating a section of portions of an aerosol-generating device and a cartridge received by the device.

In FIG. 6, the aerosol-generating device 300 and cartridge 100 are similar to those depicted in and discussed regarding FIG. 5, with similar components labeled with similar numbers. In FIG. 6, the cartridge 100 includes light guides 460 and 465. The light guide 460 at the bottom of the storage compartment 103 is configured to radiate light emitted from the light source 160 into the entire bottom surface of the cartridge in a direction generally parallel to the longitudinal axis of the storage compartment. The light guide 460 is generally parabolic and reflects light such that light from the light source 160 that hits the surface light guide 460 is reflected generally parallel to the length of the cartridge 100. The light guide 465 at the top of the storage compartment 103 is configured to direct substantially all the light transmitted through the top of the storage compartment 103 to the detector 165. The light guide 465 is generally parabolic and light that impacts the surface of the light guide 465 is reflected towards the detector 165. In some instances (not shown), the detector may be positioned at or near to the internal center of a parabolic light guide that reflects light to the center for detection.

Figure 7:
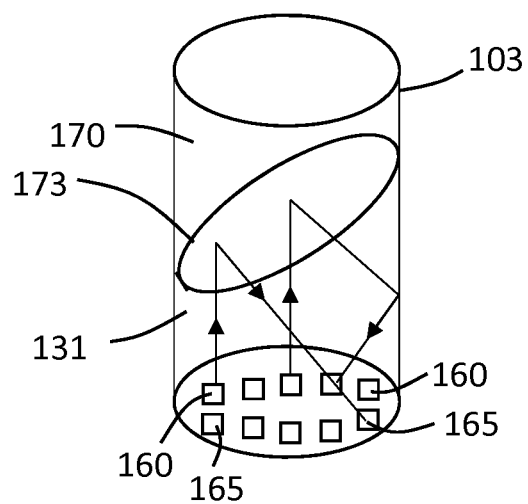
FIG. 7 is a schematic drawing illustrating a portion of a cartridge including light sources and detectors and a storage compartment.

The aerosol-generating device 300 may include an inertial sensor to determine orientation to characterize the total signal amplitude versus the proportion of fill level or volume to more accurately determine the volume or fill level of liquid composition 131 in the storage compartment 103. In FIG. 7, the cartridge includes a plurality of light sources 160 and detectors 165 positioned adjacent to the bottom of the storage compartment 103 in an alternating fashion. Having the light sources 160 and detectors 165 on the same side of the cartridge provides a more practical design because it limits the electronic components to a single side. The detectors 165 are positioned and oriented to detect light that reflects off the liquid-air interface 173 formed between the liquid composition 131 comprising an aerosol-forming substrate and air 170 in the storage compartment 103. For purposes of clarity, light is shown as being emitted from only two light sources 160 but may be emitted may any number of light sources. The signal received by all of the detectors 165 may be summed to determine the fill level or volume of the liquid composition 131. As sum the signal detected by defectors 165 provides a simple way to determine liquid volume if the orientation is known. However, the data received by the detectors 165 may be evaluated in other ways to determine the liquid volume.

Figure 8:
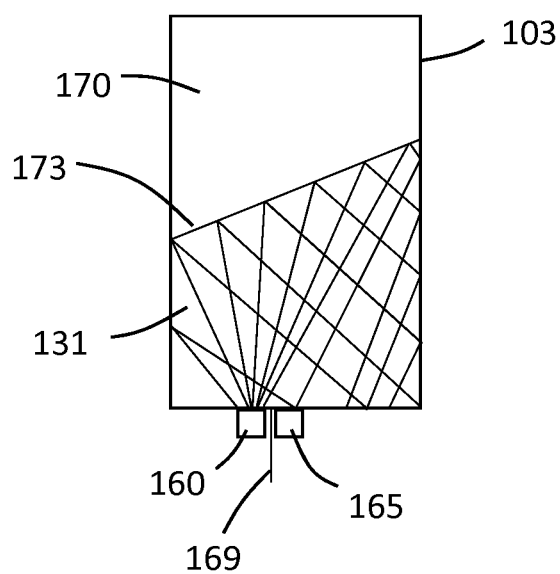
FIG. 8 is a schematic drawing illustrating a portion of a cartridge including a light source and a detector and a storage compartment.

In FIG. 8, the cartridge includes a light source 160 and detector 165 positioned adjacent to the bottom of the storage compartment 103. A separating wall 169 is positioned between the light source 160 and detector 165. The detector 165 is positioned and oriented to detect light that reflects off the liquid-air interface 173 formed between the liquid composition 131 comprising an aerosol-forming substrate and air 170 in the storage compartment 103. The interior surfaces of the storage compartment reflect light emitted by the light source. The cartridge in FIG. 8 has an advantage of simplicity. There is only one light source 160 that has wide angle of emission and only one detector 165. With the high angle of emission, it is possible for the detector 165 to receive signals in all orientation with only one light source 160. In addition, the light source 160 and the detector 165 are on the same side of the device, which also simplifies the design.

Figure 9:
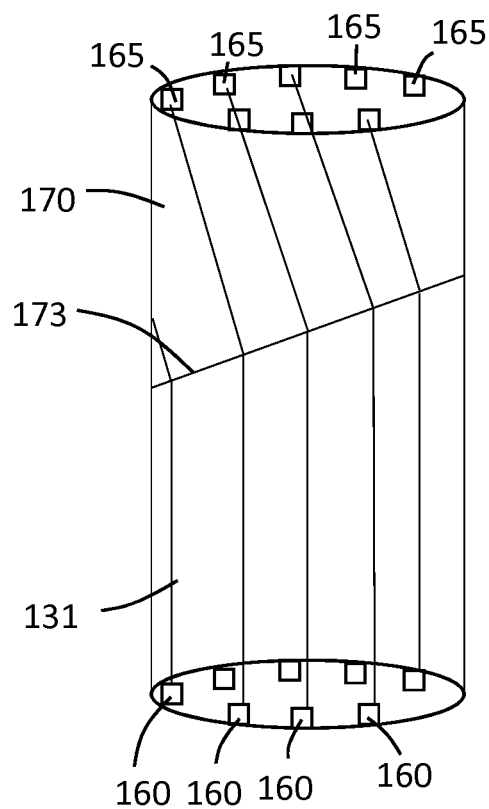
FIG. 9 is a schematic drawing illustrating a portion of a cartridge including light sources and detectors and a storage compartment.

In FIG. 9, the cartridge includes a plurality of light sources 160 positioned adjacent to the bottom of the storage compartment 103 and a plurality of detectors 165 positioned adjacent to the top of the storage compartment 103. The detectors 165 are positioned and oriented to detect light emitted from the light sources 160 through the storage compartment 103 from the bottom to the top. For a known orientation, there is a relationship between the sum of all the signals received and the liquid fill volume. The cartridge in FIG. 9 is configured to measure a signal of light transmitted through liquid-air interface 173, which may be suitable if device surrounds the top and bottom of the cartridge.

Figure 10:
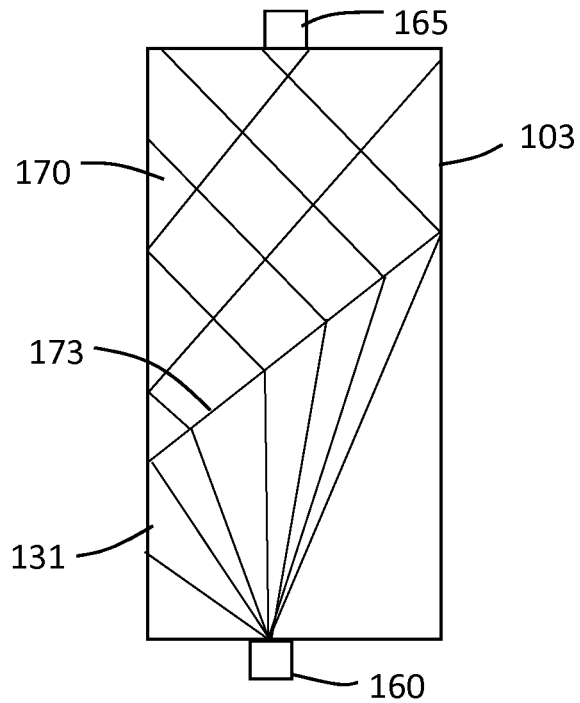
FIG. 10 is a schematic drawing illustrating a portion of a cartridge including a light source and a detector and a storage compartment.

In FIG. 10, the cartridge includes a light source 160 positioned adjacent to the bottom of the storage compartment 103 and includes a detector 165 positioned adjacent to the top of the storage compartment 103. The detector 165 is positioned and oriented to detect light emitted from the light source 160 through the storage compartment 103 from the bottom to the top. The light source is omni-directional. The interior surfaces of the storage compartment 103 reflect light emitted by the light source 160. For a known orientation, there is a relationship between the sum of all the signals received and the liquid fill volume. The cartridge in FIG. 10 is configured to measure a signal of light transmitted through liquid-air interface 173, which may be suitable if device surrounds the top and bottom of the cartridge.

All scientific and technical terms used herein have meanings commonly used in the art unless otherwise specified. The definitions provided herein are to facilitate understanding of certain terms used frequently herein.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open-ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits under certain circumstances. However, other embodiments may also be preferred under the same or other circumstances. Furthermore, the recitation of one or more preferred embodiments does not imply that other embodiments are not useful, and is not intended to exclude other embodiments from the scope of the disclosure, including the claims.

Any direction referred to herein, such as "top," "bottom," "left," "right," "upper," "lower," and other directions or orientations are described herein for clarity and brevity are not intended to be limiting of an actual device or system. Devices and systems described herein may be used in a number of directions and orientations.

The embodiments exemplified above are not limiting. Other embodiments consistent with the embodiments described above will be apparent to those skilled in the art.

The invention claimed is:

1. An aerosol-generating system, comprising:
a cartridge comprising a storage compartment configured to contain a liquid composition comprising an aerosol-forming substrate;
an aerosol-generating device configured to receive the cartridge, the aerosol-generating device comprising a power supply and control electronics operably coupled to the power supply;
a light source operably coupled to the control electronics and positioned and oriented to emit light into the storage compartment of the cartridge, wherein light emitted from the light source is absorbed by the liquid composition; and
a detector operably coupled to the control electronics and positioned and oriented to detect light emitted from the light source,
wherein the light source and the detector are both located adjacent to a same side of the storage compartment, and
wherein a surface of the storage compartment opposite the light source is configured to absorb light emitted into the storage compartment from the light source.

2. The aerosol-generating system according to claim 1, wherein the control electronics are configured to determine a fill level of the liquid composition in the storage compartment of the cartridge, or
wherein the control electronics are configured to transmit data regarding a signal detected by the detector to another device for determining the fill level of the liquid composition in the storage compartment.

3. The aerosol-generating system according to claim 1, wherein the cartridge comprises the light source and the detector,
wherein the aerosol-generating device comprises the light source and the detector,
wherein the cartridge comprises the light source and the aerosol-generating device comprises the detector, or
wherein the cartridge comprises the detector and the aerosol-generating device comprises the light source.

4. The aerosol-generating system according to claim 3, wherein, when the cartridge comprises the light source, the cartridge further comprises an exterior electrical contact operably coupled to the light source and wherein the aerosol-generating device comprises a contact operably coupled to the control electronics, wherein the contact of the aerosol-generating article and the exterior electrical contact of the cartridge are configured to electrically couple when the cartridge is received by the aerosol-generating device, and
wherein, when the cartridge comprises the detector, the cartridge further comprises an exterior electrical contact operably coupled to the detector and wherein the aerosol-generating device comprises a contact operably coupled to the control electronics, wherein the contact of the aerosol-generating article and the exterior electrical contact of the cartridge are configured to electrically couple when the cartridge is received by the aerosol-generating device.

5. The aerosol-generating system according to claim 3, wherein, when the aerosol-generating device comprises the light source, the cartridge comprises a window of material transparent to the light, the material extending from an internal surface of the storage compartment to an exterior surface of the cartridge, wherein the light source is aligned with the window when the cartridge is received by the aerosol-generating device, and
wherein, when the aerosol-generating device comprises the detector, the cartridge comprises a window of material transparent to the light, the material extending from an internal surface of the storage compartment to an exterior surface of the cartridge, wherein the detector is aligned with the window when the cartridge is received by the aerosol-generating device.

6. The aerosol-generating system according to claim 1, wherein the storage compartment of the cartridge has a length extending from a bottom of the storage compartment to a top of the storage compartment, and
wherein the light source and the detector are adjacent to the bottom of the storage compartment.

7. The aerosol-generating system according to claim 1, wherein the storage compartment of the cartridge has a length extending from a bottom of the storage compartment to a top of the storage compartment, and
wherein one of the light source and the detector is adjacent to the bottom of the storage compartment and the other of the light source and the detector is adjacent to the top of the storage compartment.

8. The aerosol-generating system according to claim 7, wherein the detector comprises a light guide configured to direct the light within the storage compartment to a surface of the detector.

9. The aerosol-generating system according to claim 7, wherein the storage compartment comprises a sidewall extending from the bottom to the top of the storage compartment, and
wherein an interior surface of the sidewall reflects the light emitted from the light source.

10. The aerosol-generating system according to claim 1, wherein the storage compartment has a sidewall extending from a bottom of the storage compartment to a top of the storage compartment, and
wherein the light source and the detector are adjacent to the sidewall between the top and the bottom of the storage compartment.

11. The aerosol-generating system according to claim 10, wherein the light source is one of a plurality of light sources and the detector is one of a plurality of detectors,
wherein each of the light sources and detectors are operably coupled to the control electronics, and
wherein the plurality of light sources and detectors are disposed about a periphery of the storage compartment substantially transverse to a longitudinal axis of the storage compartment.

12. The aerosol-generating system according to claim 11, wherein the control electronics are configured to detect a pair of a light source and a detector that are submersed in the liquid composition in the storage compartment.

13. The aerosol-generating system according to claim 1, further comprising a position sensor operably coupled to the control electronics.

14. The aerosol-generating system according to claim 13, wherein the control electronics are configured to determine a fill level of the liquid composition in the storage compartment of the cartridge based on data from the detector and from the position sensor.

15. The aerosol-generating system according to claim 13, wherein the control electronics are configured to activate the light source and the detector when the position sensor indicates that the aerosol-generating device is in a predetermined orientation.

16. A method of using an aerosol-generating system according to claim 1, the method comprising a step of inverting the aerosol-generating device to a vertical, bottom-up orientation, thereby enabling the aerosol-generating device to verify whether the storage compartment is empty or whether a small volume of liquid composition remains in the storage compartment.

17. The method according to claim 16, the method further comprising providing instructions to a user to initiate the step of inverting the aerosol-generating device.

18. An aerosol generating device, comprising:

a power supply;

control electronics operably coupled to the power supply;

a receptacle configured to receive a cartridge having a storage compartment containing a liquid composition comprising an aerosol-forming substrate;

a light source operably coupled to the control electronics and positioned and oriented to emit light into the storage compartment of the cartridge; and a detector operably coupled to the control electronics and positioned and oriented to detect the light emitted from the light source after the light has entered the storage compartment, wherein the light source and the detector are both configured to be located adjacent to a same side of a storage compartment of a cartridge when a cartridge is received within the receptacle, and wherein a surface of the storage compartment opposite the light source is configured to absorb light emitted into the storage compartment from the light source.

19. A cartridge for an aerosol-generating device, the cartridge comprising:

a storage compartment configured to house a liquid composition comprising an aerosol-forming substrate;

a light source positioned and oriented to emit light into the storage compartment;

a first contact operably coupled to the light source, wherein the first contact is positioned and oriented for electrical connection to a corresponding first contact of an aerosol-generating device when the cartridge is received in the aerosol-generating device;

a detector positioned and oriented to detect the light emitter from the light source; and a second contact operably coupled to the detector, wherein the second contact is positioned and oriented for electrical connection to a corresponding second contact of the aerosol-generating device when the cartridge is received in the aerosol-generating device, wherein the light source and the detector are both located adjacent to a same side of the storage compartment, and wherein a surface of the storage compartment opposite the light source is configured to absorb light emitted into the storage compartment from the light source.

* * * * *